(12) United States Patent
Mitchell

(10) Patent No.: US 9,603,958 B2
(45) Date of Patent: Mar. 28, 2017

(54) STERILIZATION ASSEMBLY

(71) Applicant: Deborah Mitchell, Greensboro, NC (US)

(72) Inventor: Deborah Mitchell, Greensboro, NC (US)

(*) Notice: Subject to any disclaimer, the term of this patent is extended or adjusted under 35 U.S.C. 154(b) by 0 days.

(21) Appl. No.: 14/731,083

(22) Filed: Jun. 4, 2015

(65) Prior Publication Data

US 2016/0354501 A1 Dec. 8, 2016

(51) Int. Cl.
*A61L 2/10* (2006.01)

(52) U.S. Cl.
CPC .................... *A61L 2/10* (2013.01)

(58) Field of Classification Search
USPC .................................... 250/455.11
See application file for complete search history.

(56) References Cited

U.S. PATENT DOCUMENTS

| | | | | |
|---|---|---|---|---|
| 4,896,042 A | * | 1/1990 | Humphreys | A61L 9/20 250/435 |
| 4,950,902 A | * | 8/1990 | Ritter | A61L 2/10 250/455.11 |
| 5,487,877 A | * | 1/1996 | Choi | A47K 5/00 222/192 |
| D397,886 S | | 9/1998 | Powell | |
| 6,096,264 A | | 8/2000 | Peifer | |
| 6,119,854 A | * | 9/2000 | Prentice | A46B 17/06 206/209.1 |
| 7,355,131 B2 | | 4/2008 | Pathmanathan et al. | |
| 8,778,263 B2 | * | 7/2014 | Walker | A61K 41/0019 250/454.11 |
| 2005/0109662 A1 | | 5/2005 | Kirk | |
| 2007/0075268 A1 | * | 4/2007 | Harris | A61L 2/10 250/455.11 |
| 2009/0010826 A1 | | 1/2009 | Shin | |
| 2011/0024647 A1 | | 2/2011 | Hsu | |

* cited by examiner

*Primary Examiner* — Phillip A Johnston

(57) ABSTRACT

A sterilization assembly for sterilizing personal hygiene implements includes a housing that may contain a plurality of personal hygiene implements. The housing has a top portion hingedly coupled to a bottom portion. A sterilization unit is coupled to the housing wherein the sterilization unit may sterilize the personal hygiene implements.

6 Claims, 4 Drawing Sheets

US 9,603,958 B2

STERILIZATION ASSEMBLY

BACKGROUND OF THE DISCLOSURE

Field of the Disclosure

The disclosure relates to sterilization devices and more particularly pertains to a new sterilization device for sterilizing personal hygiene implements.

SUMMARY OF THE DISCLOSURE

An embodiment of the disclosure meets the needs presented above by generally comprising a housing that may contain a plurality of personal hygiene implements. The housing has a top portion hingedly coupled to a bottom portion. A sterilization unit is coupled to the housing wherein the sterilization unit may sterilize the personal hygiene implements.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
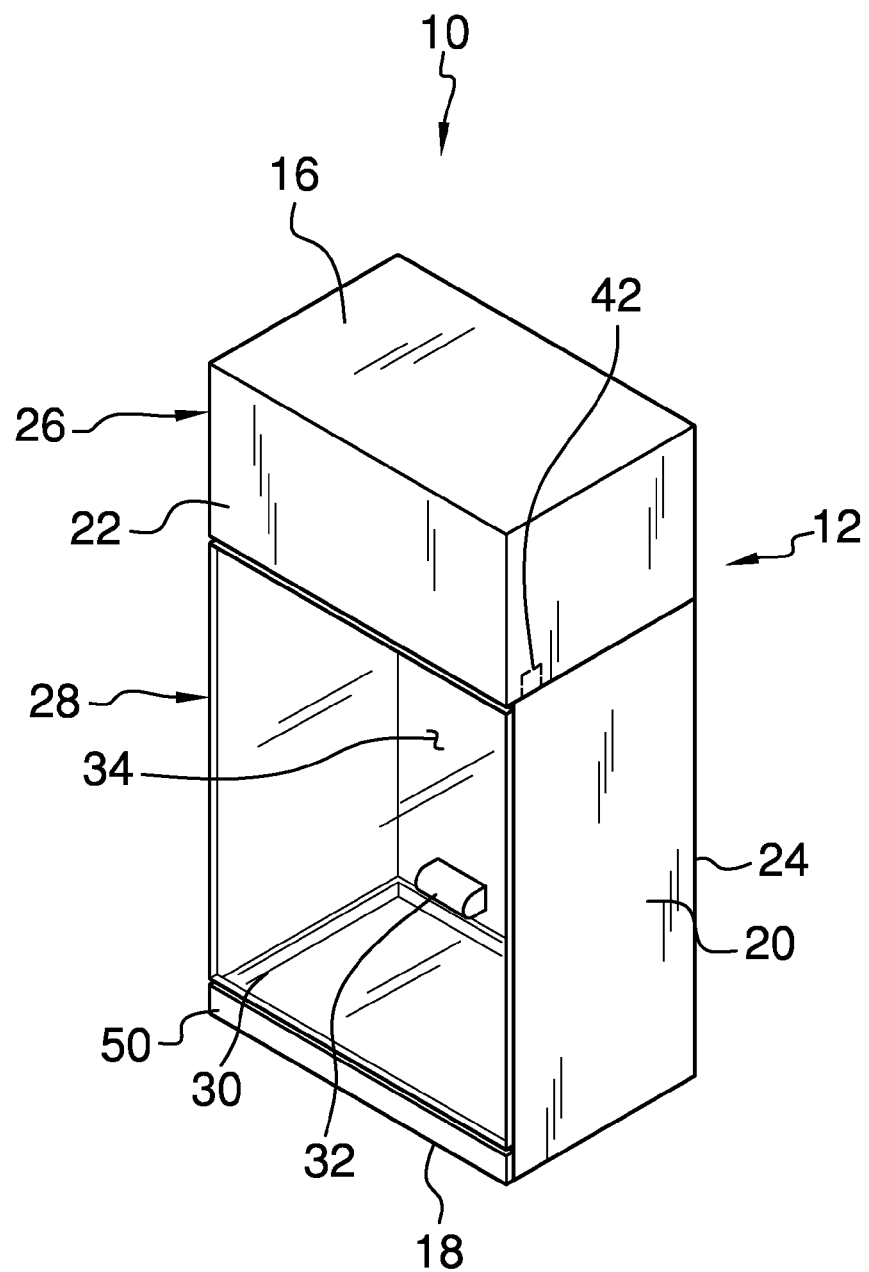
FIG. 1 is a front perspective view of a sterilization assembly according to an embodiment of the disclosure.
Figure 2:
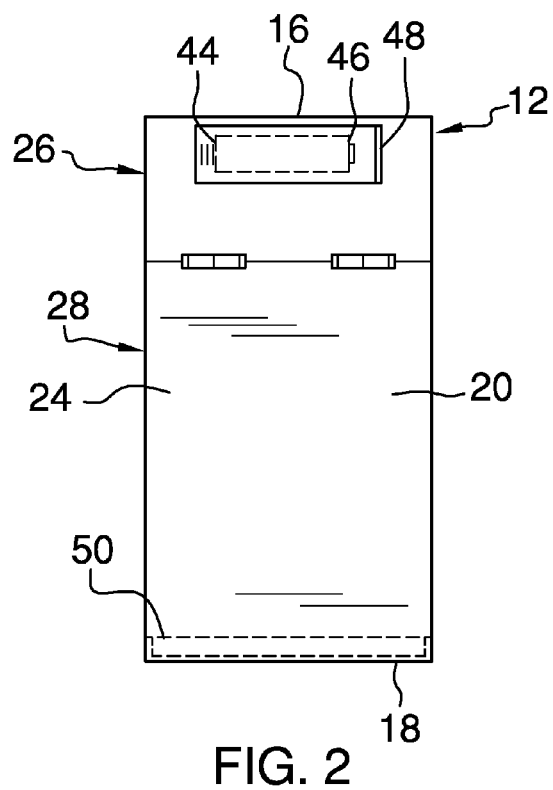
FIG. 2 is a back view of an embodiment of the disclosure.
Figure 3:
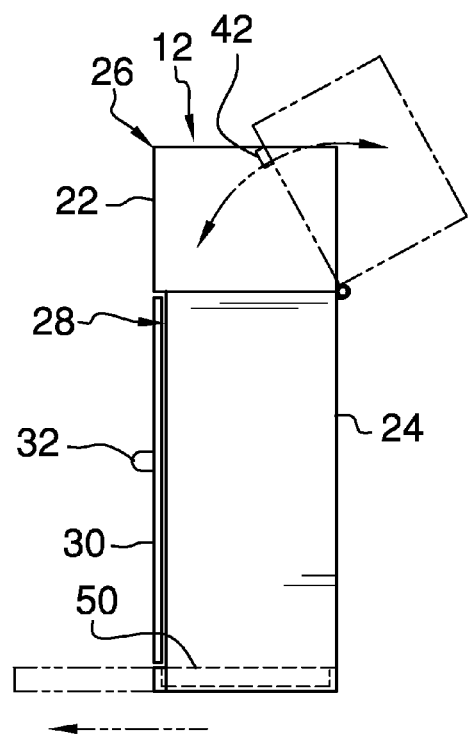
FIG. 3 is a left side view of an embodiment of the disclosure.
Figure 4:
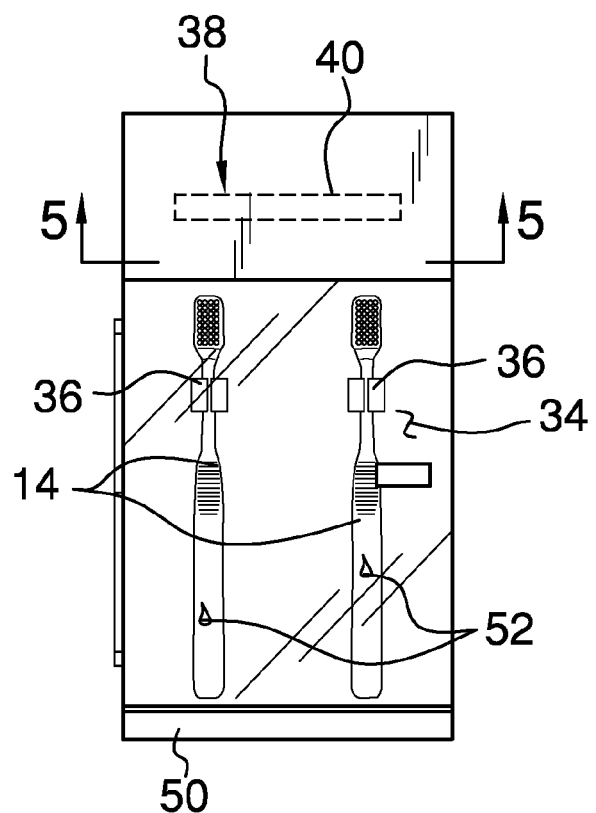
FIG. 4 is a front view of an embodiment of the disclosure.
Figure 5:
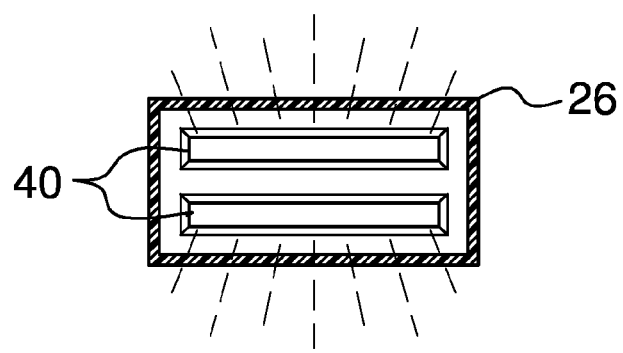
FIG. 5 is a cross sectional view of an embodiment of the disclosure.
Figure 6:
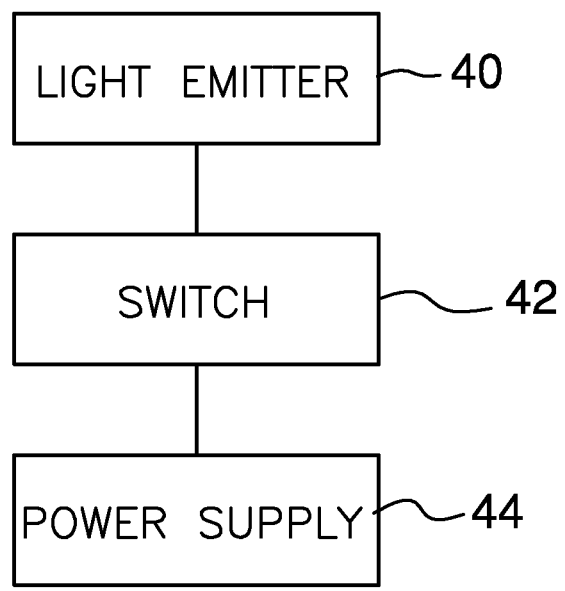
FIG. 6 is a schematic view of an embodiment of the disclosure.

With reference now to the drawings, and in particular to FIGS. 1 through 6 thereof, a new sterilization device embodying the principles and concepts of an embodiment of the disclosure and generally designated by the reference numeral 10 will be described.

As best illustrated in FIGS. 1 through 6, the sterilization assembly 10 generally comprises a housing 12 that may contain a plurality of personal hygiene implements 14. Each of the personal hygiene implements 14 may comprise toothbrush or the like. The housing 12 has a top wall 16, a bottom wall 18 and a peripheral wall 20 extending between the top wall 16 and the bottom wall 18. The peripheral wall 20 has a front side 22 and a back side 24. The housing 12 is substantially hollow and the housing 12 has a top portion 26 hingedly coupled to a bottom portion 28. The back side 24 corresponding to the top portion 26 is hingedly coupled to the back side 24 corresponding to the bottom portion 28. The top portion 26 is positionable in an open position having the top portion 26 being spaced from the bottom portion 28. The top portion 26 is positionable in a closed position having the top portion 26 abutting the bottom portion 28.

The front side 22 corresponding to the bottom portion 28 is open wherein the bottom portion 28 may receive the personal hygiene implements 14. A door 30 is hingedly coupled to the housing 12 and the door 30 is positioned on the front side 22 corresponding to the bottom portion 28. The door 30 is positionable in a closed position to cover the front side 22 corresponding to the bottom portion 28. The door 30 is positionable in an open position to access an interior of the bottom portion 28. The door 30 may be comprised of a translucent material and the door 30 may comprised of a material that restricts ultraviolet radiation from passing through the door 30. A handle 32 is coupled to the door 30 wherein the handle 32 may be gripped.

The back side 24 corresponding to the bottom portion 28 has an inner surface 34. A pair of clips 36 is provided and each of the clips 36 is attached to the inner surface 34 of the back side 24. Each of the clips 36 is spaced apart from each other and each of the clips 36 is positioned closer to the top portion 26 than the bottom wall 18. Each of the clips 36 receives an associated one of the personal hygiene implements 14 thereby retaining the personal hygiene implements 14 in an upright orientation within the housing 12.

A sterilization unit 38 is coupled to the housing 12 wherein the sterilization unit 38 may sterilize the personal hygiene implements 14. The sterilization unit 38 comprises a light emitter 40 that is positioned within the top portion 26. The light emitter 40 is positioned to emit radiation into the bottom portion 28 wherein the light emitter 40 sterilizes the personal hygiene implements 14. The light emitter 40 may comprise a UV light emitter that emits electromagnetic radiation having a wavelength that is less than approximately 254 nm.

A switch 42 is coupled to the top portion 26. The switch 42 is positioned on the front side 22 corresponding to the top portion 26 such that the switch 42 engages the front side 22 corresponding to the bottom portion 28 when the top portion 26 is positioned in the closed position. The switch 42 is electrically coupled to the light emitter 40 wherein the switch 42 actuates the light emitter 40 when the top portion 26 is positioned in the closed position. The switch 42 de-actuates the light emitter 40 when the top portion 26 is positioned in the open position.

A power supply 44 is positioned within the top portion 26 and the power supply 44 is electrically coupled to the switch 42. The power supply 44 comprises at least one battery 46. A battery cover 48 is removably coupled to the back side 24 corresponding to the top portion 26. The power supply 44 is positioned beneath the battery cover 48.

A tray 50 is slidably coupled to the housing 12 and the tray 50 is positioned on the front side 22 corresponding to the bottom portion 26. The tray 50 is positioned adjacent to the bottom wall 18 wherein the tray 50 may capture fluid 52 dripping from the personal hygiene implements 14. The tray 50 is slidably removable outwardly from the bottom portion 28 wherein the tray 50 may be emptied of the fluid 52 and the fluid 52 may be water.

In use, the top portion 26 is positioned in the open position and each of the personal hygiene implements 14 is positioned within an associated one of the clips 36. The door 30 is closed and the top portion 26 is positioned in the closed position such that the sterilization unit 38 is actuated. The top portion 26 is positioned in the open position and the door 30 is opened to remove the personal hygiene implements 14 from the housing 12. The tray 50 is removed and emptied when the tray 50 becomes full of the fluid 52.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A sterilization assembly configured to contain and sterilize a personal hygiene implement, said assembly comprising:
   a housing configured to contain a plurality of personal hygiene implements, said housing having a top portion hingedly coupled to a bottom portion, said housing having a top wall, a bottom wall and a peripheral wall extending between said top wall and said bottom wall, said housing being substantially hollow, said top portion being positionable in an open position having said top portion being spaced from said bottom portion, said top portion being positionable in a closed position having said top portion abutting said bottom portion;
   a door being hingedly coupled to said housing, said door being positioned on said front side corresponding to said bottom portion, said door being positionable in a closed position to cover said front side corresponding to said bottom portion, said door being positionable in an open position to access an interior of said bottom portion:
   a sterilization unit being coupled to said housing wherein said sterilization unit is configured to sterilize the personal hygiene implements and said sterilization unit comprises a light emitter being positioned within said top portion, said light emitter being positioned to emit radiation into said bottom portion wherein said light emitter is configured to sterilize the personal hygiene implements; and
   a tray being slidably coupled to said housing, said tray being positioned on said front side corresponding to said bottom portion, said tray being positioned adjacent to said bottom wall wherein said tray is configured to capture fluid dripping from the personal hygiene, said tray being slidably removable outwardly from said bottom portion wherein said tray is configured to be emptied of the fluid.

2. The assembly according to claim 1, wherein said peripheral wall has a front side, said front side corresponding to said bottom portion being open wherein said bottom portion is configured to receive the personal hygiene implements.

3. The assembly according to claim 1, wherein a handle being coupled to said door wherein said handle is configured to be gripped.

4. The assembly according to claim 1, further comprising:
   said housing having a front side; and
   a switch being coupled to said top portion, said switch being positioned on said front side corresponding to said top portion such that said switch engages said front side corresponding to said bottom portion when said top portion is positioned in said closed position, said switch being electrically coupled to said light emitter wherein said switch actuates said light emitter when said top portion is positioned in said closed position, said switch deactivating said light emitter when said top portion is positioned in said open position.

5. The assembly according to claim 4, further comprising a power supply being positioned within said top portion, said power supply being electrically coupled to said switch, said power supply comprising at least one battery.

6. A sterilization assembly configured to contain and sterilize a personal hygiene implement, said assembly comprising:
   a housing configured to contain a plurality of personal hygiene implements, said housing having a top wall, a bottom wall and a peripheral wall extending between said top wall and said bottom wall, said housing being substantially hollow, said housing having a top portion hingedly coupled to a bottom portion, said top portion being positionable in an open position having said top portion being spaced from said bottom portion, said top portion being positionable in a closed position having said top portion abutting said bottom portion, said peripheral wall having a front side, said front side corresponding to said bottom portion being open wherein said bottom portion is configured to receive the personal hygiene implements;
   a door being hingedly coupled to said housing, said door being positioned on said front side corresponding to said bottom portion, said door being positionable in a closed position to cover said front side corresponding to said bottom portion, said door being positionable in an open position to access an interior of said bottom portion;
   a handle being coupled to said door wherein said handle is configured to be gripped;
   a sterilization unit being coupled to said housing wherein said sterilization unit is configured to sterilize the personal hygiene implements, said sterilization unit comprising:
   a light emitter being positioned within said top portion, said light emitter being positioned to emit radiation into said bottom portion wherein said light emitter is configured to sterilize the personal hygiene implements,
   a switch being coupled to said top portion, said switch being positioned on said front side corresponding to said top portion such that said switch engages said front side corresponding to said bottom portion when said top portion is positioned in said closed position, said switch being electrically coupled to said light emitter wherein said switch actuates said light emitter when said top portion is positioned in said closed position, said switch de-actuating said light emitter when said top portion is positioned in said open position, and a power supply being positioned within said top portion, said power supply being electrically coupled to said switch, said power supply comprising at least one battery; and a tray being slidably coupled to said housing, said tray being positioned on said front side corresponding to said bottom portion, said tray being positioned adjacent to said bottom wall wherein said tray is configured to capture fluid dripping from the personal hygiene, said tray being slidably removable outwardly from said bottom portion wherein said tray is configured to be emptied of the fluid.

\* \* \* \* \*